United States Patent
Moser et al.

(10) Patent No.: US 11,633,400 B2
(45) Date of Patent: Apr. 25, 2023

(54) CRYSTALLINE SALT COMPRISING 5-METHYL-(6S)-TETRAHYDROFOLIC ACID AND 4-(2-HYDROXYETHYL)-MORPHOLINE

(71) Applicant: MERCK PATENT GMBH, Darmstadt (DE)

(72) Inventors: Rudolf Moser, Schaffhausen (CH); Viola Groehn, Dachsen (CH); Ruth Boehni Stamm, Stein Am Rhein (CH); Fritz Blatter, Reinach (CH); Martin Szelagiewicz, Basel (CH)

(73) Assignee: MERCK PATENT GMBH, Darmstadt (DE)

( * ) Notice: Subject to any disclaimer, the term of this patent is extended or adjusted under 35 U.S.C. 154(b) by 290 days.

(21) Appl. No.: 17/258,051

(22) PCT Filed: Jul. 2, 2019

(86) PCT No.: PCT/EP2019/067692
§ 371 (c)(1),
(2) Date: Jan. 5, 2021

(87) PCT Pub. No.: WO2020/007834
PCT Pub. Date: Jan. 9, 2020

(65) Prior Publication Data
US 2021/0220366 A1 Jul. 22, 2021

(30) Foreign Application Priority Data
Jul. 6, 2018 (EP) .................................. EP18182277

(51) Int. Cl.
*A61K 31/519* (2006.01)
*C07D 487/04* (2006.01)

(52) U.S. Cl.
CPC .......... *A61K 31/519* (2013.01); *C07D 487/04* (2013.01); *C07B 2200/13* (2013.01)

(58) Field of Classification Search
CPC . A61K 31/519; C07D 487/04; C07B 2200/13
See application file for complete search history.

(56) References Cited

U.S. PATENT DOCUMENTS

| 6,441,168 B1 | 8/2002 | Müller et al. |
| 2016/0207925 A1 | 7/2016 | Fracchia |

FOREIGN PATENT DOCUMENTS

WO    WO 2017/007756 A1 * 1/2017 ........... C07D 403/12

OTHER PUBLICATIONS

International search report PCT/EP2019/067698 dated Sep. 13, 2019 (pp. 1-3).

* cited by examiner

*Primary Examiner* — Valerie Rodriguez-Garcia
*Assistant Examiner* — David M Shim
(74) *Attorney, Agent, or Firm* — Millen, White, Zelano and Branigan, P.C.; Harry B. Shubin

(57) ABSTRACT

The present invention refers to a crystalline salt comprising 5-methyl-(6S)-tetrahydrofolic acid and 4-(2-hydroxyethyl)-morpholine wherein the molar ratio of 5-methyl-(6S)-tetrahydrofolic acid to 4-(2-hydroxyethyl)-morpholine is from 1:0.3 to 1:2.0 (in mol/mol) and/or hydrates and/or solvates thereof as well as to a process of obtaining the same.

17 Claims, 3 Drawing Sheets

CRYSTALLINE SALT COMPRISING 5-METHYL-(6S)-TETRAHYDROFOLIC ACID AND 4-(2-HYDROXYETHYL)-MORPHOLINE

The present invention is directed to a crystalline salt comprising 5-methyl-(6S)-tetrahydrofolic acid (N-[4-[[(2-amino-1,4,5,6,7,8-hexahydro-5-methyl-4-oxo-(6S)-pteridinyl)methyl]amino]benzoyl]-L-glutamic acid) and 4-(2-hydroxyethyl)-morpholine and a process of obtaining the same.

Tetrahydrofolates are predominantly used as the calcium salt of 5-formyltetrahydrofolic acid (leucovorin and levoleucovorin), as the calcium salt of 5-methyltetrahydrofolic acid (Metafolin®), or as the sulfate salt of 5,10-methylenetetrahydrofolic acid (Modufolin®). Most prominent fields of use are for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

The calcium salt of 5-methyl-(6S)-tetrahydrofolic acid is used in particular as a drug and as a food additive, as a vitamin preparation, for the prevention of neural tube defects, for the treatment of depressive illnesses, and for influencing the homocysteine level.

5-Methyl-(6S)-tetrahydrofolic acid and salts thereof are known to be extremely unstable. In particular they are highly susceptible to oxidation [see also A. L. Fitzhugh, Pteridines 4 (4), 187-191 (1993) in this respect] and therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid and salts thereof.

U.S. Pat. No. 6,441,168 B1 discloses alkaline earth salts of 5-methyltetrahydrofolic acid, particularly the calcium salt, its crystallization and its use. The drawback of such crystalline calcium salt of 5-methyl-(6S)-tetrahydrofolic acid is that it exists in its crystalline form in up to four polymorphic modifications. Therefore, the process of manufacturing the crystalline calcium salt of 5-methyl-(6S)-tetrahydrofolic acid has to be controlled very precisely. Additionally, the crystalline calcium salt of 5-methyl-(6S)-tetrahydrofolic acid of U.S. Pat. No. 6,441,168 B1 typically contains in the crystal lattice of all its polymorphic forms at least one but up to four equivalents of water per equivalent of 5-methyl-(6S)-tetrahydrofolic acid.

New crystal forms of a pharmaceutically useful compound offer an opportunity to improve the performance profile of a pharmaceutical and/or vitamin/medical food products. It widens the reservoir of materials a formulation scientist has available for designing a new dosage forms with improved characteristics.

The technical problem underlying the present invention is the provision of a crystalline form comprising 5-methyl-(6S)-tetrahydrofolic acid which overcomes the drawbacks of the crystalline calcium salt of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

For the sake of stability of tetrahydrofolates it is always the aim to provide a compound which has a low water absorption upon storage and which can be dried sufficiently during manufacturing. In addition, drug substances that do not absorb high amounts of water under ambient conditions are highly desired. Particularly desired are substances that do not change their water content when the ambient relative humidity changes because large changes of the water content due to change of the relative humidity of the environment make it more difficult to achieve a great precision with the respect to the dosage form.

The technical problem underlying the present invention is solved by a crystalline salt comprising 5-methyl-(6S)-tetrahydrofolic acid and 4-(2-hydroxyethyl)-morpholine wherein the molar ratio of 5-methyl-(6S)-tetrahydrofolic acid to 4-(2-hydroxyethyl)-morpholine is from 1:0.3 to 1:2.0 (in mol/mol) and/or hydrates and/or solvates thereof.

The solid form of the present invention possesses improved pharmacological characteristics, thus offering enhanced possibilities to modulate and design improved drug products. Compared with the crystalline polymorphic forms of the calcium salt of 5-methyl-(6S)-tetrahydrofolic acid known in the art the water adsorption of the crystalline salt of 5-methyl-(6S)-tetrahydrofolic acid and 4-(2-hydroxyethyl)-morpholine is significantly lower leading to substantially improved control over the target dosage form level in the drug product because the change of the amounts of adsorbed water under changing relative humidity conditions is significantly less pronounced. Another advantageous aspect of the crystalline salt of 5-methyl-(6S)-tetrahydrofolic acid and 4-(2-hydroxyethyl)-morpholine is that a high chemical and optical purity of 5-methyl-(6S)-tetrahydrofolic acid can be achieved in one single crystallization step. Additionally, the crystalline salt comprising 5-methyl-(6S)-tetrahydrofolic acid and 4-(2-hydroxyethyl)-morpholine exists in its crystalline form in one clearly defined polymorphic modification. Therefore, the process of manufacturing the crystalline salt comprising 5-methyl-(6S)-tetrahydrofolic acid and 4-(2-hydroxyethyl)-morpholine does not require very precise control of crystallisation conditions.

Preferably, the crystalline salt has a molar ratio of 5-methyl-(6S)-tetrahydrofolic acid to 4-(2-hydroxyethyl)-morpholine from 1:0.5 to 1:1.5 (in mol/mol).

Even more preferred, the molar ratio of 5-methyl-(6S)-tetrahydrofolic acid to 4-(2-hydroxyethyl)-morpholine is from 1:0.75 to 1:1.25 (in mol/mol).

Most preferred, the ratio of 5-methyl-(6S)-tetrahydrofolic acid to 4-(2-hydroxyethyl)-morpholine is approximately 1:1 (in mol/mol).

Preferably, the salt of the present invention is the crystalline salt of 5-methyl-(6S)-tetrahydrofolic acid and 4-(2-hydroxyethyl)-morpholine and has a PXRD pattern with at least one characteristic peak (expressed in 2θ±0.2° 2θ (CuKα radiation)) selected from the following peaks located at 14.2, 14.8, 19.7, 20.0, and 20.6.

More preferred, the salt of the present invention is the crystalline salt of 5-methyl-(6S)-tetrahydrofolic acid and 4-(2-hydroxyethyl)-morpholine and has a PXRD pattern with at least three characteristic peaks (expressed in 2θ±0.2° 2θ (CuKα radiation)) selected from the following peaks located at 14.2, 14.8, 19.7, 20.0, and 20.6.

Even more preferred, the salt of the present invention is the crystalline salt of 5-methyl-(6S)-tetrahydrofolic acid and 4-(2-hydroxyethyl)-morpholine and has a PXRD pattern with peaks (expressed in 2θ±0.2° 2θ (CuKα radiation)) selected from the following peaks located at 14.2, 14.8, 19.7, 20.0, and 20.6.

Even more preferred, the salt of the present invention is the crystalline salt of 5-methyl-(6S)-tetrahydrofolic acid and 4-(2-hydroxyethyl)-morpholine and has a PXRD pattern with at least one characteristic peak (expressed in 2θ±0.2° 2θ (CuKα radiation)) selected from the following peaks located at 4.9, 12.2, 14.2, 14.8, 15.1, 15.3, 17.4, 19.7, 20.0, 20.6, 23.6, 24.9, and 28.1.

Most preferred, the salt of the present invention is the crystalline salt of 5-methyl-(6S)-tetrahydrofolic acid and 4-(2-hydroxyethyl)-morpholine and has a PXRD pattern substantially as shown in FIG. 1.

The aforementioned salt of 5-methyl-(6S)-tetrahydrofolic acid and 4-(2-hydroxyethyl)-morpholine may have at least 99 wt % or more chemical and/or stereoisomerical purity.

Comparing the salt of 5-methyl-(6S)-tetrahydrofolic acid and 4-(2-hydroxyethyl)-morpholin with the calcium salt of 5-methyl-(6S)-tetrahydrofolic shows that the water content of the salt of 5-methyl-(6S)-tetrahydrofolic acid and 4-(2-hydroxyethyl)-morpholin changes less than 2% (Example 2, FIG. 2) within the most relevant range between 20% and 80% while the water content for the calcium salt of 5-methyl-(6S)-tetrahydrofolic acid changes by more than 4% (Reference example 2, FIG. 3). This result is very surprising to a person skilled in the art and could not be expected when considering the teaching of U.S. Pat. No. 6,441,168 B1. Moreover, the salt of 5-methyl-(6S)-tetrahydrofolic acid and 4-(2-hydroxyethyl)-morpholine of the present invention clearly solves the technical problem underlying the present invention.

It is advantageous having a salt comprising 5-methyl-(6S)-tetrahydrofolic with a very low water content and especially a low tendency to absorb/desorb water, e.g. when handling the substance for compounding in a temperature/humidity-controlled environment or in tropical countries, where the relative humidity generally is very high.

Thus, the salt of the present invention exhibits improved storage stability even under these conditions. These improved properties were not derivable bearing the teaching of U.S. Pat. No. 6,441,168 B1 in mind.

5-methyl-(6S)-tetrahydrofolic acid is poorly soluble in water. The thermodynamically stable form of the calcium salt (Form III) is known to exhibit an aqueous solubility of about 2.5 mg/ml and the solubility of the metastable Form I is about 10 mg/ml at room temperature. Under certain pH conditions, in particular when the pH of the environments is lower than the equilibrium pH of a given salt, the salts can potentially disproportionate into free acid and as a consequence, the solubility decreases substantially. Therefore, thermodynamic solubilities of the claimed salts at about neutral to lower pH values are inaccessible due to slow salt disproportionation (formation of poorly soluble free acid). However, the bioavailability is dominated by kinetic effects. Administration of a solid form of a drug product is followed by dissolution and after the first dissolution step the drug is diluted by body fluids and distributed. Therefore, the kinetic solubility is a key parameter that influences the bioavailability because the initially dissolved drug substance is readily diluted and transported. For the salt of 5-methyl-(6S)-tetrahydrofolic acid and 4-(2-hydroxyethyl)-morpholine is was surprisingly found that the kinetic solubility is improved by a factor of about three versus the known (metastable Form I) of the calcium salt. The difference in the kinetic solubility of the salt of the present invention to the thermodynamically stable form of the calcium salt (Form III) would presumably even be larger. Thus, temporarily a much higher drug substance concentration can be achieved.

A further aspect of the present invention is a process for obtaining the crystalline salt comprising 5-methyl-(6S)-tetrahydrofolic acid and 4-(2-hydroxyethyl)-morpholine comprising the steps of:

a) providing a mixture of 5-methyl-(6S)-tetrahydrofolic acid and 4-(2-hydroxyethyl)-morpholine, optionally in a suitable solvent or a mixture of solvents b) crystallizing c) optionally adding more solvent or mixture of solvents; and d) isolating the obtained crystals.

Preferably, the molar ratio of 5-methyl-(6S)-tetrahydrofolic acid and 4-(2-hydroxyethyl)-morpholine in step a) is in the range of from 1:1 to 1:3.

Further preferred, the solvent is water, an alcohol and/or a ketone.

In step b) and/or c) seed crystals may be added.

As the crystalline salt comprising 5-methyl-(6S)-tetrahydrofolic acid and 4-(2-hydroxyethyl)-morpholine exists in its crystalline form just in one clearly defined polymorphic modification the process of manufacturing the crystalline salt does not require very precise control of crystallisation conditions.

A further aspect of the present invention is a pharmaceutical composition, food additive and/or preparation comprising the crystalline salt of 5-methyl-(6S)-tetrahydrofolic acid and 4-(2-hydroxyethyl)-morpholine and optionally one or more acceptable excipients is also part of the invention. The pharmaceutical composition may have the form of tablets, capsules, oral liquid preparations, powders, lyophilisates, granules, lozenges, reconstitutable powders, injectable or infusable solutions or suspensions or suppositories. Also, the pharmaceutical composition may further comprise at least one additional therapeutic agent. Pharmaceutical compositions according to the present invention are suitable for all modes of administration, preferably for oral, parenteral, intramuscular, intraspinal, intrathecal, periodontal, topical or rectal administration.

A further aspect of the present invention is the use of the crystalline salt comprising 5-methyl-(6S)-tetrahydrofolic acid and 4-(2-hydroxyethyl)-morpholine as constituent for the production of drugs and/or as a food additive.

Preferably, the crystalline salt comprising 5-methyl-(6S)-tetrahydrofolic acid and 4-(2-hydroxyethyl)-morpholine is used in the treatment in homocysteine-lowering, of anemia, neural tube defects, cardiovascular diseases, depression, Alzheimer's disease, cognitive impairment and osteoporosis and/or dietary management of low plasma and/or low red blood cell and/or low cerebrospinal fluid and/or low peripheral or central nervous system folate.

In summary, the profile of properties offered by the salt of 5-methyl-(6S)-tetrahydrofolic acid and 4-(2-hydroxyethyl)-morpholine of the present invention is advantageous for use in medicaments or as food additive. Especially, the low change in water content in an environment from 20% to 80% relative humidity and the higher kinetic solubility could not been foreseen by the skilled artisan.

Figure 3:
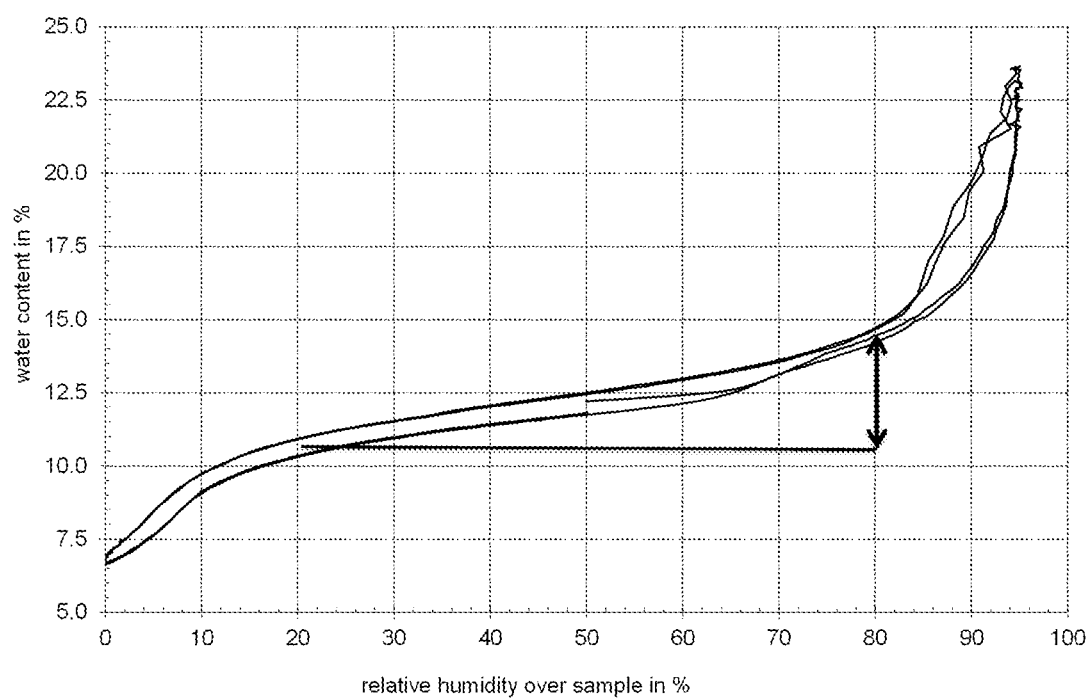

FIG. 3: DVS measurements of the calcium salt with 5-methyl-(6S)-tetrahydrofolic acid. They-axis shows the water content of the samples. The vertical arrow illustrates the change of water content in the range from 20 to 80% relative humidity which is about 4%.

EXAMPLES

Powder X-Ray Diffraction

Stoe Stadi P equipped with a Mythen1 K Detector; Cu-Kα1 radiation; standard measurement conditions: transmission; 40 kV and 40 mA tube power; curved Ge monochromator; 0.02° 2θ step size, 48 s step time, 1.5-50.5° 2θ scanning range; detector mode: step scan; 1° 2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

TG-FTIR

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

DVS

DVS measurements are typically performed with an SPS11-100n "Sorptions Prüfsystem" from ProUmid (formerly "Projekt Messtechnik"), August-Nagel-Str. 23, 89079 Ulm (Germany).

Figure 1:
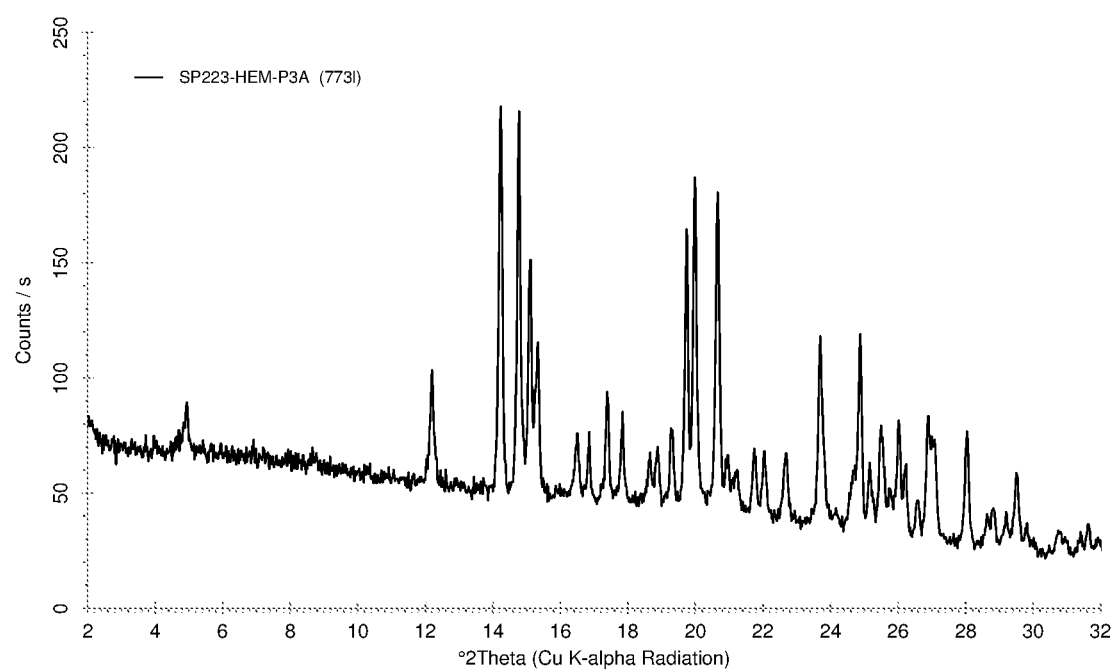
FIG. 1: Powder X-ray diffraction pattern of the crystalline salt comprising 5-methyl-(6S)-tetrahydrofolic acid salt and 4-(2-hydroxyethyl)-morpholine.
Figure 2:
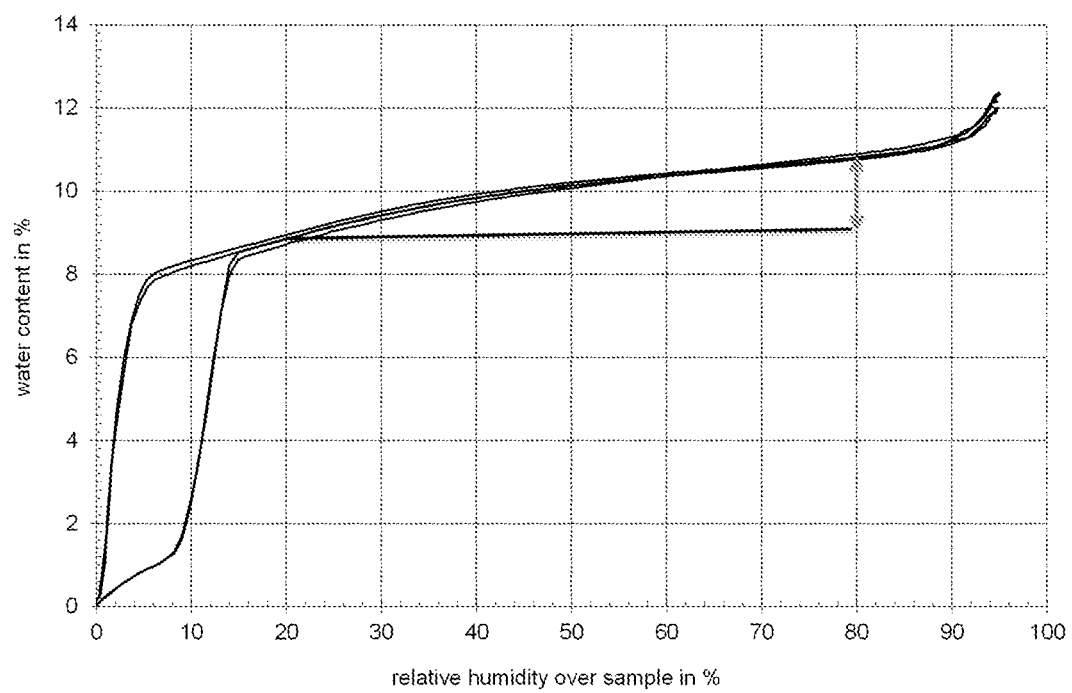
FIG. 2: DVS measurements of the crystalline salt comprising 5-methyl-(6S)-tetrahydrofolic acid salt and 4-(2- hydroxyethyl)-morpholine. The y-axis shows the water content of the samples. The vertical arrow illustrates the change of water content in the range from 20 to 80% relative humidity which is about 2%.

DVS measurements were conducted as follows: The sample was placed on an aluminum holder on top of a microbalance and allowed to equilibrate at 50% RH before starting the pre-defined humidity program:

(1) two hours kept at 50% constant relative humidity (RH) then
(2) raised RH to 95% at a rate of 5% per hour
(3) maintained RH at 95% for five hours
(4) reduced to 0% RH at a rate of 5% per hour
(5) maintained RH at 0% for five hours
(6) raised RH to 95% at a rate of 5% per hour
(7) maintained RH at 95% for five hours
(8) reduced to 0% RH at a rate of 5% per hour
(9) maintained RH at 0% for five hours
(10) raised to 50% RH at a rate of 5% per hour
(11) maintained RH at 50% for about one hour Example 1: Preparation of Crystalline Salt of 5-methyl-(6S)-tetrahydrofolic Acid with 4-(2-hydroxyethyl)-morpholine 4.763 grams of 5-methyl-(6S)-tetrahydrofolic acid monohydrate (assay 5-methyltetrahydrofolic acid 97.65% w/w) were weighed into a glass flask equipped with a magnetic stirrer bar. 9.5 mL of water and 4.76 mL of 4-(2-hydroxyethyl)-morpholine (Aldrich #H28203) were added. After stirring at room temperature for about 2 minutes a brown clear solution was formed. While stirring the solution at room temperature, 95 mL of acetone was added slowly within about 2.5 hours. The suspension formed was stirred at room temperature for about 23 hours. The suspension was then filtered with a fritted glass filter (porosity P4) and the filter cake was air dried at ambient temperature. 100 mL of ethanol was added to the filter cake and the wash solution was pulled through the filter by vacuum suction. The wash step was repeated with another 100 mL of ethanol. The filter cake was then air dried for about 0.5 hour (air was drawn through the fritted glass filter). About 5.6 grams of solid product was obtained and characterized by HPLC, powder X-ray diffraction, H-NMR spectroscopy and TG-FTIR. Powder X-ray diffraction showed that the material was crystalline with a PXRD pattern as depicted in FIG. 1 with peak locations as presented in Table 1.

Table 1 2-theta angles, d-spacings and qualitative intensities for the salt of 5-methyl-(6S)-tetrahydrofolic acid and 4-(2-hydroxyethyl)-morpholine according to Example 1. Vs=very strong, s=strong, m=medium, w=weak, and vw=very weak in intensity. It should be noted that intensity values can vary substantially due to preferred orientation effects.

| °2-theta | d-spacings [Å] | intensity (qualitative) |
| --- | --- | --- |
| 4.9 | 17.9 | m |
| 12.2 | 7.2 | s |
| 14.2 | 6.2 | vs |
| 14.8 | 5.98 | vs |
| 15.1 | 5.86 | s |
| 15.3 | 5.78 | s |
| 16.5 | 5.37 | s |
| 16.9 | 5.25 | m |
| 17.4 | 5.10 | s |
| 17.8 | 4.97 | s |
| 18.7 | 4.74 | m |
| 19.3 | 4.60 | s |
| 19.7 | 4.50 | vs |
| 20.0 | 4.44 | vs |
| 20.6 | 4.30 | vs |
| 21.0 | 4.24 | s |
| 21.2 | 4.19 | m |
| 21.7 | 4.09 | s |
| 22.0 | 4.04 | s |
| 22.7 | 3.91 | s |
| 23.6 | 3.76 | s |
| 24.9 | 3.58 | s |
| 25.1 | 3.54 | m |
| 25.5 | 3.49 | s |
| 25.8 | 3.46 | m |
| 26.1 | 3.41 | s |
| 26.6 | 3.35 | m |
| 26.9 | 3.31 | s |
| 28.1 | 3.18 | s |
| 29.4 | 3.03 | m |
| 32.5 | 2.75 | m |

Example 2: Preparation of Crystalline Salt of 5-methyl-(6S)-tetrahydrofolic Acid with 4-(2-hydroxyethyl)-morpholine 47.63 grams of 5-methyl-(6S)-tetrahydrofolic acid monohydrate (assay 5-methyl-(6S)-tetrahydrofolic acid 97.99% w/w, 6S-diastereoisomer: 98.0%) were suspended at room temperature in 95 mL of water. 47.6 mL of 4 (2-hydroxyethyl)-morpholine were added while the temperature was rising to approximately 50° C. without cooling. The mixture was cooled down to room temperature. To the dark brown clear solution 950 mL of acetone were added slowly within about 2.5 hours. The suspension formed was stirred at room temperature for about 23 hours. The suspension was then filtered with a fritted glass filter (porosity G3) and the filter cake was washed with 1000 mL of ethanol. The so obtained light beige solid was dried over night at 40° C./10 mbar. About 52.4 grams of solid product were obtained and characterized by HPLC, powder X-ray diffraction and $^1$H-NMR spectroscopy. HPLC analysis showed a purity of 98.7% area, 6S-diastereoisomer: 98.7% Powder X-ray diffraction showed that the material was crystalline with a PXRD pattern as depicted in FIG. 1 with peak locations as presented in Table 1.

Example 3: Hygroscopicity and Water Content (DVS Experiments)

TG-FTIR analysis of a sample of the salt of 5-methyl-(6S)-tetrahydrofolic acid and 4-(2-hydroxyethyl)-morpholine according to Example 1 showed that the sample contained about 8.9% w/w of water. This value was determined by TG-FTIR at a relative humidity of about 35%. This sample was examined by dynamic water vapor sorption analysis (DVS) within the relative humidity range from 0 to 95% r.h. DVS measurements were conducted as described above.

Comparing the result for the salt of 5-methyl-(6S)-tetrahydrofolic acid and 4-(2-hydroxyethyl)-morpholine with the result for the calcium salt of 5-methyl-(6S)-tetrahydrofolic acid shows that the water content of the salt of 5-methyl-(6S)-tetrahydrofolic acid and 4-(2-hydroxyethyl)-morpholine changes about 2% within the range from 20% to 80% relative humidity while the change for the calcium salt of 5-methyl-(6S)-tetrahydrofolic acid is about 4% (Reference example 2). Furthermore, the example shows that the water content of the salt of 5-methyl-(6S)-tetrahydrofolic acid and 4-(2-hydroxyethyl)-morpholine at 50% relative humidity is about 10% and that the compound absorbs about 2% of additional water when the relative humidity is increased from 50% to 95%. 50% r.h. is a typical ambient relative humidity condition for a middle European summer day; however, when drug products are stored in a bathroom the relative humidity can temporarily reach at least 95%.

Example 3: Kinetic Solubility of the Salt of 5-methyl-(6S)-tetrahydrofolic Acid and 4-(2-hydroxyethyl)-morpholine 27.1 mg of the salt of 5-methyl-(6S)-tetrahydrofolic acid and 4-(2-hydroxyethyl)-morpholine prepared according to Example 1 were weighed into a 7 mL glass vial with a screw cap and 0.5 mL of purified/de-ionized water was added to the solid using an adjustable volumetric pipette. The mixture was vigorously agitated at room temperature and after a few seconds all solid was dissolved and a clear solution was obtained. This means that for the salt of 5-methyl-(6S)-tetrahydrofolic acid and 4-(2-hydroxyethyl)-morpholine more than 54 mg per mL water can be readily dissolved. This corresponds to an immediate kinetic solubility which is greater than 37 mg of 5-methyl-(6S)-tetrahydrofolic acid per mL of water.

Reference Example 1: Kinetic Solubility of the Calcium Salt of 5-methyl-(6S)-Tetrahydrofolic Acid 42.5 mg of the anhydrous form of the crystalline 5-methyl-(6S)-tetrahydrofolic acid calcium salt was weighed into a 7 mL glass vial with a screw cap. 2.00 mL of purified/de-ionized water was added to the solid using an adjustable volumetric pipette. The mixture was vigorously agitated at room temperature for one minute. After one minute a suspension was observed. The suspension was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours. Subsequently drying was completed at 50° C. under vacuum (10 to 20 mbar) for about 13 hours. The solubility was determined by gravimetric evaluation of the solid residue. The solubility was 9.0 mg of 5-methyl-(6S)-tetrahydrofolic acid per mL of water.

Reference Example 2: Hygroscopicity and Water Content of the Calcium Salt of 5-methyl-(6S)-tetrahydrofolic Acid TG-FTIR analysis of a sample of 5-methyl-(6S)-tetrahydrofolic acid calcium salt showed that the sample contained about 12.4% of water. This sample was examined by dynamic water vapor sorption analysis (DVS) within the relative humidity range from 0 to 95% r.h. DVS measurements were conducted as described above.

The result is presented in FIG. 3 and shows that within the most relevant range from 20% to 80% the water content for the calcium salt of 5-methyl-(6S)-tetrahydrofolic acid changes by about 4%. Furthermore, the reference example shows that the water content of the calcium salt of 5-methyl-(6S)-tetrahydrofolic acid at 50% relative humidity is about 12.4% and that the compound absorbs more than 10% of additional water when the relative humidity is increased from 50% to 95%.

The invention claimed is:

1. A crystalline salt comprising 5-methyl-(6S)-tetrahydrofolic acid and 4-(2-hydroxyethyl)-morpholine wherein the molar ratio of 5-methyl-(6S)-tetrahydrofolic acid to 4-(2-hydroxyethyl)-morpholine is in the range of 1:0.3 to 1:2.0 (in mol/mol) or a hydrate or solvate thereof.

2. The crystalline salt of claim 1, wherein the molar ratio of 5-methyl-(6S)-tetrahydrofolic acid to 4-(2-hydroxyethyl)-morpholine is in the range of 1:0.5 to 1:1.5 (in mol/mol) or a hydrate or solvate thereof.

3. The crystalline salt of claim 1, wherein the molar ratio of 5-methyl-(6S)-tetrahydrofolic acid to 4-(2-hydroxyethyl)-morpholine is in the range of 1:0.75 to 1:1.25 (in mol/mol) or a hydrate or solvate thereof.

4. The crystalline salt of claim 1, wherein the ratio of 5-methyl-(6S)-tetrahydrofolic acid to 4-(2-hydroxyethyl)-morpholine is approximately 1:1 (in mol/mol) and/or hydrates and/or solvates thereof.

5. The crystalline salt of claim 1, wherein the crystalline salt of 5-methyl-(6S)-tetrahydrofolic acid and 4-(2-hydroxyethyl)-morpholine has a PXRD pattern with at least one characteristic peak, which is expressed in 2θ±0.2° 2θ with CuKα radiation, selected from the following peaks located at 14.2, 14.8, 19.7, 20.0, and 20.6.

6. The crystalline salt of claim 1, wherein the crystalline salt of 5-methyl-(6S)-tetrahydrofolic acid and 4-(2-hydroxyethyl)-morpholine has a PXRD pattern with at least three characteristic peaks, which is expressed in 2θ±0.2° 2θ with CuKα radiation, selected from the following peaks located at 14.2, 14.8, 19.7, 20.0, and 20.6.

7. The crystalline salt of claim 1, wherein the crystalline salt of 5-methyl-(6S)-tetrahydrofolic acid and 4-(2-hydroxyethyl)-morpholine has a PXRD pattern with at least one characteristic peak, which is expressed in 2θ±0.2° 2θ with CuKα radiation, selected from the following peaks located at 4.9, 12.2, 14.2, 14.8, 15.1, 15.3, 17.4, 19.7, 20.0, 20.6, 23.6, 24.9, and 28.1.

8. The crystalline salt of claim 1, wherein the crystalline salt of 5-methyl-(6S)-tetrahydrofolic acid and 4-(2-hydroxyethyl)-morpholine has a PXRD pattern substantially as shown in FIG. 1.

9. The crystalline salt of claim 1 having at least 99 wt % or more chemical and/or stereoisomerical purity.

10. A process for obtaining the crystalline salt comprising 5-methyl-(6S)-tetrahydrofolic acid and 4-(2-hydroxyethyl)-morpholine according to claim 1, comprising the steps of:
   a) providing a mixture of 5-methyl-(6S)-tetrahydrofolic acid and 4-(2-hydroxyethyl)-morpholine, optionally in a suitable solvent or a mixture of solvents
   b) crystallizing
   c) optionally adding more solvent or mixture of solvents; and
   d) isolating the obtained crystals.

11. The process of claim 10, wherein the molar ratio of 5-methyl-(6S)-tetrahydrofolic acid and 4-(2-hydroxyethyl)-morpholine in step a) is in the range of 1:1 to 1:3.

12. The process of claim 10, wherein the solvent is water, an alcohol and/or a ketone.

13. The process of claim 10, wherein seed crystals are added in step b) and/or step c).

14. A pharmaceutical composition, food additive and/or preparation comprising the crystalline salt of 5-methyl-(6S)-tetrahydrofolic acid and 4-(2-hydroxyethyl)-morpholine according to claim 1 and optionally one or more acceptable excipients.

15. The pharmaceutical composition according to claim 14, which is in the form of a tablet, capsule, oral liquid preparation, powder, lyophilisate, granule, lozenge, reconstitutable powder, injectable or infusable solution or suspension or suppository.

16. The pharmaceutical composition according to claim 14 further comprising at least one additional therapeutic agent.

17. The pharmaceutical composition according to claim 14, which is a pharmaceutical composition for oral, parenteral, intramuscular, intraspinal, intrathecal, periodontal, topical or rectal administration.

* * * * *